(12) United States Patent
Abramovich et al.

(10) Patent No.: US 11,573,173 B2
(45) Date of Patent: Feb. 7, 2023

(54) REAL TIME MONITORING OF SUBSTANCE CONCENTRATION, PARTICULARLY OF AMMONIA, IN FISH PONDS AND LIKE ENVIRONMENTS

(71) Applicants: Ariel Scientific Innovations Ltd., Ariel (IL); The State of Israel, Ministry of Agriculture & Rural Development, Agricultural Research Organization (ARO) (Volcani Center), Rishon-LeZion (IL); The State of Israel, Ministry of Agriculture & Rural Development, Rishon-LeZion (IL)

(72) Inventors: Amir Abramovich, Herzliya (IL); Nafttaly Goldshleger, Rosh HaAyin (IL); Sheenan Harpaz, Rehovot (IL); Aharon Greenberg, Mishmar HaSharon (IL); Alexander Shulzinger, Ariel (IL)

(73) Assignees: Ariel Scientific Innovations Ltd., Ariel (IL); The State of Israel, Ministry of Agriculture & Rural Development, Agricultural Research Organization (ARO) (Volcani Center), Rishon-LeZion (IL); The State of Israel, Ministry of Agriculture & Rural Development, Rishon-LeZion (IL)

( * ) Notice: Subject to any disclaimer, the term of this patent is extended or adjusted under 35 U.S.C. 154(b) by 238 days.

(21) Appl. No.: 16/638,178

(22) PCT Filed: Aug. 10, 2018

(86) PCT No.: PCT/IL2018/050889
§ 371 (c)(1),
(2) Date: Feb. 11, 2020

(87) PCT Pub. No.: WO2019/030764
PCT Pub. Date: Feb. 14, 2019

(65) Prior Publication Data
US 2020/0363326 A1    Nov. 19, 2020

Related U.S. Application Data

(60) Provisional application No. 62/544,003, filed on Aug. 11, 2017.

(51) Int. Cl.
*G01N 21/3504*    (2014.01)
*G01N 1/14*       (2006.01)
(Continued)

(52) U.S. Cl.
CPC .......... *G01N 21/3504* (2013.01); *G01N 1/14* (2013.01); *G01N 30/64* (2013.01);
(Continued)

(58) Field of Classification Search
CPC ...... G01N 21/3504; G01N 1/14; G01N 30/64; G01N 33/0054; G01N 33/18;
(Continued)

(56) References Cited

U.S. PATENT DOCUMENTS

| | | |
|---|---|---|
| 3,929,003 A | 12/1975 | LLewellyn |
| 2004/0034480 A1 | 2/2004 | Binder |
| 2013/0285821 A1* | 10/2013 | Nakamura ........... G08B 21/182 340/603 |

FOREIGN PATENT DOCUMENTS

| | | |
|---|---|---|
| JP | 2006-267047 | 10/2006 |
| WO | WO 03/100393 | 12/2003 |

(Continued)

OTHER PUBLICATIONS

International Search Report and the Written Opinion dated Nov. 15, 2018 From the International Searching Authority Re. Application No. PCT/IL2018/050889. (11 Pages).
(Continued)

*Primary Examiner* — David P Porta
*Assistant Examiner* — Meenakshi S Sahu

(57) ABSTRACT

Apparatus and method for detecting a dissolved gaseous impurity in an aqueous environment, comprises a tube for isolating liquid surface, or a sampler for obtaining a liquid sample from the aqueous environment, a vacuum pump located to exert a vacuum, leaving the surface to evaporate into the vacuum; and a holding compartment for holding evaporated gas which may then be analyzed using electrochemical or spectroscopic methods. The apparatus is useful for detecting levels of ammonia in fish ponds or indeed any impurity that may be dissolved in the water.

21 Claims, 12 Drawing Sheets

(51) Int. Cl.
| | |
|---|---|
| *G01N 30/64* | (2006.01) |
| *G01N 33/00* | (2006.01) |
| *G01N 33/18* | (2006.01) |
| *G01N 21/35* | (2014.01) |
| *G01N 30/02* | (2006.01) |

(52) U.S. Cl.
CPC ......... *G01N 33/0054* (2013.01); *G01N 33/18* (2013.01); *G01N 2021/3595* (2013.01); *G01N 2030/025* (2013.01)

(58) Field of Classification Search
CPC ..... G01N 2021/3595; G01N 2030/025; G01N 1/4022; G01N 33/182; G01N 21/031; G01N 2001/1418; G01N 1/12; G01N 21/3577
See application file for complete search history.

(56) References Cited

FOREIGN PATENT DOCUMENTS

| | | |
|---|---|---|
| WO | WO 2016/116306 | 7/2016 |
| WO | WO 2019/030764 | 2/2019 |

OTHER PUBLICATIONS

Notification of Office Action and Search Report dated Aug. 31, 2022 From the State Intellectual Property Office of the People's Republic of China Re. Application No. 201880066323.7. (9 Pages).
Translation Dated Sep. 13, 2022 of Notification of Office Action dated Aug. 31, 2022 From the State Intellectual Property Office of the People's Republic of China Re. Application No. 201880066323. 7. (4 Pages).

* cited by examiner

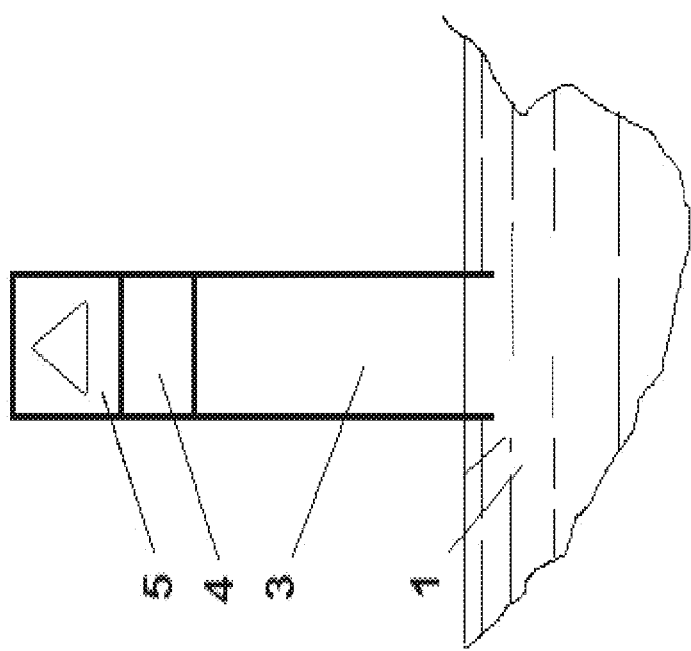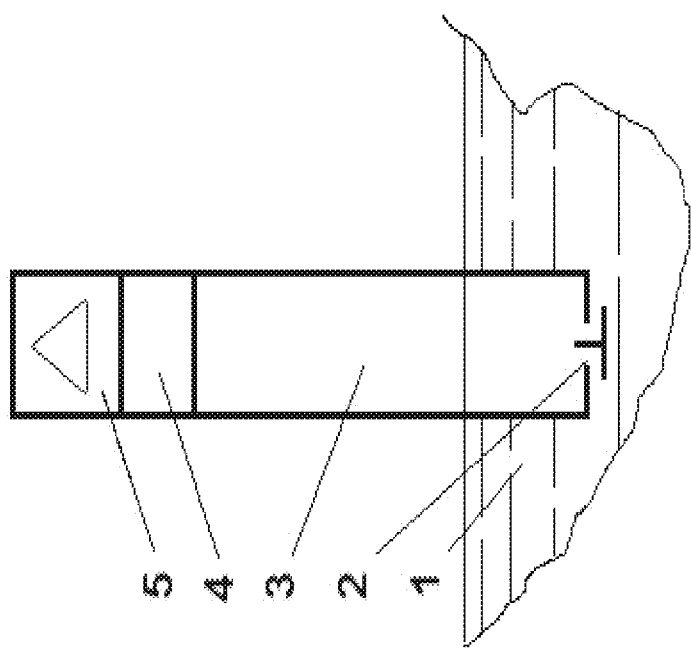

REAL TIME MONITORING OF SUBSTANCE CONCENTRATION, PARTICULARLY OF AMMONIA, IN FISH PONDS AND LIKE ENVIRONMENTS

RELATED APPLICATIONS

This application is a National Phase of PCT Patent Application No. PCT/IL2018/050889 having International filing date of Aug. 10, 2018, which claims the benefit of priority under 35 USC § 119(e) of U.S. Provisional Patent Application No. 62/544,003 filed on Aug. 11, 2017. The contents of the above applications are all incorporated by reference as if fully set forth herein in their entirety.

FIELD AND BACKGROUND OF THE INVENTION

The present invention, in some embodiments thereof, relates to monitoring of substance concentration in solutions, more particularly but not exclusively to contaminants dissolved in water, and particularly relating to aquaculture and contaminants such as ammonia in fish ponds.

The need to produce greater amounts of food sources due to the growing population in the world is among the driving forces behind the intensification of the agriculture and aquaculture production systems. Currently there are a number of methods utilized to culture fish, ranging from extensive production ponds in which the density of the fish is around or below one fish per 1 $m^3$ and depends on natural means to maintain the water quality, to systems which are capable of recycling the water and producing about 100 times more fish per 1 $m^3$. The improvements in this field raise the need for close monitoring of the quality of the water used in the production systems. One of the factors of utmost importance in aquaculture is the level of ammonia ($NH_3$) concentrations in the pool water.

Ammonia is considered highly toxic to fish and even low concentrations of 0.06 ppm are enough to create chronic stress for the fish which leads to gills and kidney tissue damage, while concentrations of 0.6 ppm are already considered lethal for some fish species, and some species may be sensitive to concentrations as low as 0.1 ppm. Ammonia appears in the water as an end process of de-amination of proteins. It can be either a product of the fish metabolites, or may come from unconsumed food in the water. Since fish foods typically contain high protein levels (up to 60% protein), the possibility that ammonia levels may become toxic is of constant concern. The levels of ammonia in the water can change rapidly and are dependent on many factors that exist in the water. Plants, algae and bacteria consume ammonia as an energy source and therefore can reduce its level in the water. There are a-biotic factors that influence the toxicity, such as pH levels, temperature, alkalinity and salinity. In order to maintain fish health and growth, it is imperative to monitor ammonia levels on a daily basis.

Existing devices that monitor ammonia levels can be divided into wet systems which measure ammonia dissolved in liquid and dry systems which monitor the ammonia in the gas phase. Most of the test systems to measure Ammonia in water are based on chemical reactions. Many of them count the total ammonia nitrogen (TAN) in the water as the level of $NH_4^+$ molecules, and then calculate the $NH_3$ concentrations using the pH level and temperature charts $NH_{3\ (aq)} + H_2O_{(l)} \leftrightarrow NH_4^+{}_{(aq)} + OH^-{}_{(aq)}$. These systems, which are easy to use, do not take into account changes that occur during the day, such as for example: algae activity during daylight, and are therefore limited in their scope. Most of these systems are based on colorimetric results which are subjective, and can be influenced by the background color of the pond's water. There are other systems that can monitor ammonia levels in real time utilizing the electric charge of the $NH_4^+$ molecule, and calculating the ammonia level based on the pH levels and temperature. But these systems tend to produce false results when other soluble ions are present in the pond water.

SUMMARY OF THE INVENTION

The present embodiments use spectroscopy on an evaporate into an effective vacuum of a sample of the water being tested to determine the quantity of ammonia or any other designated substance. Furthermore, the present embodiments may be used to analyze the concentration of other ingredients in liquids such as blood, urine, sweat, spittle, drinks of all kind and more according to spectral signature of the ingredients. Particularly the Oxygen concentration in ponds and in other liquids can be carried out using this method based on the well-known absorption line of oxygen at 60 GHz.

According to an aspect of some embodiments of the present invention there is provided apparatus for detecting a dissolved gaseous impurity in an aqueous environment, comprising:
 a vacuum pump located to exert a vacuum onto an isolated liquid surface, leaving the surface to evaporate into the vacuum; and
 a holding compartment for holding evaporated gas from the sample.

Embodiments may comprise a spectroscopy unit to detect spectroscopic signals of the evaporated gas, thereby to identify a gaseous impurity or a concentration of the gaseous impurity in the aqueous environment.

The spectroscopy unit may comprise a radiation source and a detector and may be built into the holding unit.

The spectroscopy unit may be configured to use Fourier Transform Infra-Red (FTIR) spectroscopy.

An embodiment may comprise an electrochemical detector unit configured to identify the gaseous impurity.

The sampler may be vacuum resistant, and may comprise a valve at one end, the valve being openable to obtain the liquid sample and closeable prior to applying the vacuum to a surface of the sample from the other end.

In an embodiment, the holding compartment is removable for remote spectroscopic analysis.

In an embodiment, the detector unit is configured to detect ammonia or a concentration of ammonia or other aqueous substances.

In an embodiment, the aqueous environment is an aquaculture environment.

According to a further aspect of the present invention there is provided a method of detecting dissolved gaseous impurities in an aqueous environment, comprising:
 obtaining a sample volume of the aqueous environment;
 applying a vacuum above a surface of the sample volume;
 allowing the sample volume to evaporate into the vacuum; and
 applying measurement to the evaporate to detect a gaseous impurity.

The measurement may be obtained using electrochemical detection.

The measurement may be obtained using spectroscopy, for example Fourier Transform Infra-Red (FTIR) spectroscopy.

The present method may be used to detect a concentration of ammonia, and the aqueous environment may be an aquaculture environment.

Alternatively, the aqueous environment may be a liquid for human consumption.

In embodiments multiple measurement devices may be floated on a body of water and may transmit measurements to a central location to provide real time monitoring of the body of water. The devices may include a transmitter and a location detector such as a GPS. The devices may be moored or free floating, and may be battery or solar powered. The devices may be Internet of Things (IOT) devices for adaptable connectivity.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description provided with the drawings makes apparent to those skilled in the art how embodiments of the invention may be practiced.

In the drawings:

FIG. 1A is a simplified diagram illustrating pond water sampling according to an embodiment of the present invention;

FIG. 1B is a simplified diagram illustrating a variation of the pond water sampling of FIG. 1A;

DESCRIPTION OF SPECIFIC EMBODIMENTS OF THE INVENTION

Figure 2A:
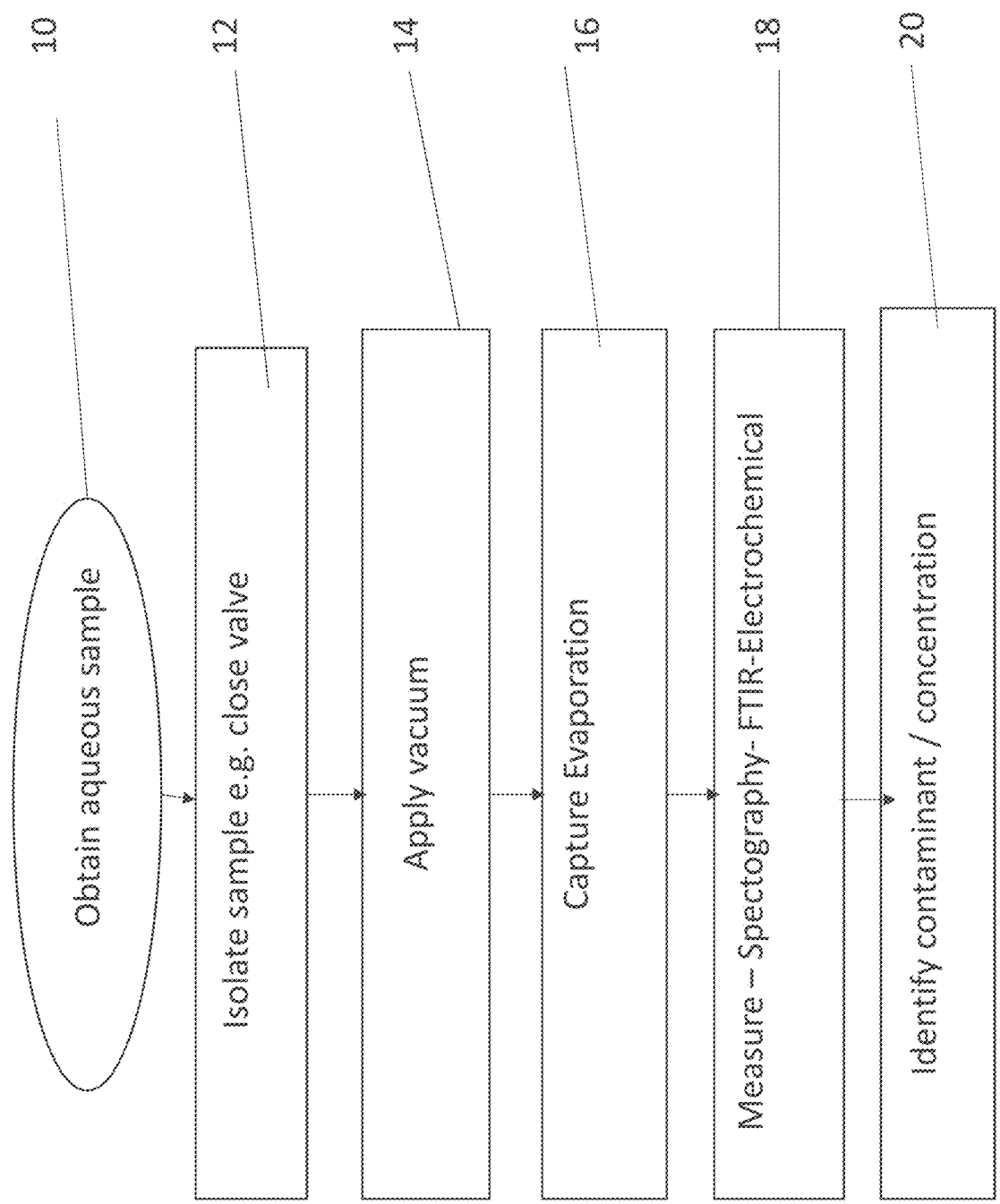
FIG. 2A is a flow chart of a sampling methodology usable in the present embodiments.

The present invention, in some embodiments thereof, relates to monitoring of substance concentration in solutions, more particularly but not exclusively to contaminants dissolved in water, and particularly relating to aquaculture and contaminants such as ammonia in fish ponds.

A broad variety of gas transmission cells are available for the analysis of gas and vapor phase components using infrared optical spectroscopy. These range from short path length gas cells for percent level concentration measurement, to long pathlength gas cells (or multi pass cell) for part-per-billion concentrations. Options include fixed and variable pathlength gas cells, as well as ambient temperature and heated gas cells. Gas is passed through the cells and analyzed using spectroscopy techniques.

However, gas transmission cells are designed for gasses, not for liquids, and even if the pond water were evaporated, spectroscopy techniques may not be efficient for identifying a small component in water due to large attenuation due to water and poor Signal to Noise Ratio (SNR) received from the water.

The present embodiments describe a method and apparatus to monitor the Ammonia concentration changes in fish ponds which allows gas cells to be used. The method is based on monitoring the spectral signature of pure Ammonia ($NH_3$) in the MIR and FIR spectral range. The water of the pond is evaporated, not by heating, but by using a vacuum pump and transferred to a gas cell where spectroscopy or other measurement techniques such as electrochemical techniques may be used. An advantage of using a vacuum pump is that for many substances, only a weak vacuum is needed to improve evaporation and thus less energy is needed than for heating the sample to the extent needed to get the same effect.

With spectroscopy, a light beam interacts with the evaporated gas, and, as described below, a linear relationship has been found between the concentration of Ammonia during the evaporation process and the detected signal. Ammonia concentrations in the order of as low as 1 or even 0.1 ppm are detected and the levels are confirmed by conventional methods. Higher sensitivities are achieved if longer interaction paths are used in longer path gas cells such as multiple path cells. The advantages of the present embodiments may include being a direct measure of ammonia rather than the indirect calculations used today, a higher accuracy and real time operation.

The present embodiments may thus provide a real time innovative method to monitor changes of toxic Ammonia in fish pond water.

As mentioned, the present embodiments may use spectroscopy, and may use a comparison between the well-known absorption lines of pure Ammonia in the MIR (Mid Infra-Red) and FIR (Far Infra-Red) bands with lines detected in evaporate taken from the pond's water. Interaction between the evaporated gases from the pond water and electromagnetic radiation in the spectral range of MIR and FIR may yield a spectral signature. Subsequent comparison between the measured spectral signatures and absorption lines of the evaporate with the absorption lines of pure ammonia can then yield the concentration of Ammonia in the pond water. Using the present method may thus allow for direct measurement of $NH_3$ concentration in the pond in real-time.

Further embodiments may provide a technique to help overcome the problems associated with detecting very low concentrations by increasing the interaction length in the measurement cell.

Gas cells have been used in the past. The present embodiments may evaporate the water into a vacuum and then measure the vacuum cell for the contents using spectroscopy. Ammonia or other substances cannot be accurately measured in the water environment itself using spectroscopic techniques due to large attenuation and poor SNR. The present embodiments may detect and measure the unique absorption line of ammonia, or other substances in the water, in particular substances that evaporate preferentially to water at the temperature used. The present embodiments allow for evaporation from the water, or other aqueous solution, into the vacuum cell environment. Inside the vacuum cell there are two components: a radiation source and sensor, which are suitable for the absorption line range of the ammonia or other required substance in the aqua solution. The vacuum inside the cell may be achieved by using a vacuum pump of a kind similar to that found in electric blood pressure measurement devices. Where the transmission measurements of the radiation decrease, it means that part of the radiation power has been absorbed by the ammonia molecules in the evaporate present in the vacuum cell.

The present embodiments may provide one or more of the following advantages:

A real time or continuous measurement of ammonia concentration in water at levels of less than 1 PPM.

Direct measurement of ammonia, by contrast with the prior art in which the measurement is indirect, based on calculations and temperature and pH of the water, and thus loses accuracy.

Very little maintenance is required, as compared with the devices according to the current art, where the instruments generally require daily maintenance and constant replacement.

Cleaning may be rarely if ever required.

The results may generally exceed the accuracy ranges of current devices.

With some minor modifications, the present embodiments may be used to measure various substances, harmful or otherwise, that may be present in aqueous solution, in fish ponds and any other environment. Substances that may be monitored in this way include oxygen concentration, nitrite concentration, sulphide concentration, nitrate concentration, organophosphates, alcohol and other substances that may be present in aqueous solutions.

As well as aquaculture, the present embodiments may be applicable to fields such as: drinking water monitoring, the food industry, body fluid diagnostics and monitoring, including urine tests, blood tests, say for alcohol or glucose concentrations, or to analyze sweat, even breath monitoring, and bacteria detection particularly by looking for bacterial waste products, and the embodiments may indeed be used in any other cases in which spectroscopy may detect distinct and known spectral lines in an evaporate.

The embodiment required to measure ammonia may be relatively simple and thus inexpensive. Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways.

Referring now to the drawings, FIG. 1A is a simplified diagram which illustrates a first embodiment of the present invention. In FIG. 1A a sampling tube is inserted into pond water 1. A sampling tube includes a valve 2 leading to a tube 3. The valve closes to isolate a sample, and a partial vacuum is formed when pump 5 sucks air away from the surface of the water within the tube. The vacuum leads from the water sample surface via holding compartment 4 to the vacuum pump 5 which is the vacuum source.

The tube 3 may be inserted to a predetermined depth in the pond water 1, and a sample volume of water enters the tube. The valve 2 closes, and the pump 5 produces the vacuum above the water surface. The vacuum is then filled by gas molecules evaporating from the water surface, including ammonia gas if present in the water. The extracted gas is analyzed by spectrometric, electrochemical or other methods. Then the valve 2 opens, and the described cycle may be repeated as further samples are taken. The samples may be measured on site by including a gas cell with compartment 4, or compartment 4 may be a removable compartment and the sample may be taken away for offsite measurement.

In a variation, the pond water sample may be taken using a simple beaker or the like and added to the sampling device attached to the vacuum pump at a remote location where the measurement is carried out.

In a further variation, the sampling device may include a built in pump as shown as well as a portable spectrometer, so that all measurements are carried out on site.

More generally, FIG. 1A illustrates apparatus for detecting a dissolved gaseous impurity in an aqueous environment, which includes but is not limited to ammonia in fish farming ponds.

Tube 3 forms a sample reservoir which may hold a liquid sample of the aqueous environment, namely in general the pond water. The pump 5 is a vacuum pump and is located to exert a vacuum onto the surface of the liquid sample, leaving the sample to evaporate gaseous molecules into the vacuum. A holding compartment 4 holds the evaporated gas from the sample for subsequent measurement, or may itself comprise a gas cell for measurement.

Measurement may be carried out using spectroscopy. A spectroscopy unit may detect spectroscopic signals in the evaporated gas molecules, and allow a gaseous impurity or a concentration of the gaseous impurity to be identified. The spectroscopy unit may comprise a radiation source and a detector. The spectroscopy may use the Fourier Transform Infra-Red (FTIR) technique, as discussed in greater detail herein below.

The spectroscopy unit may initially be calibrated on a known sample of the substance to be detected.

Alternatively, measurement may be carried out using an electrochemical detector unit. The detector unit allows a chromatography column to be formed and then detects electrical signals.

As discussed, the sampler has a valve 2 at one end that is lowered into the water being sampled so that a sample can be taken and the valve closed. The vacuum pump 5 may be located on the opposite side of compartment 4 to apply a vacuum to the upper surface of the sample once the valve 2 has been closed. The sample then evaporates into the vacuum and a sample of the evaporating molecules may be obtained in the chamber 4 for subsequent analysis.

The compartment 4 is removable in some embodiments for remote spectroscopic analysis. Thus a series of ponds on a fish farm may be sampled one after the other using different compartments which are then labelled and removed and taken away for sampling.

The detector unit may be explicitly programmed to detect a specific contaminant such as ammonia, or to detect the concentration of the specific contaminant.

The aqueous environment 1 may in embodiments be an aquaculture environment.

Reference is now made to FIG. 1B which is a variation of the sampling tube 3 of FIG. 1A. In FIG. 1B, a valve is dispensed with, since in order to form a vacuum only a surface isolated by surrounding walls is needed. The tube 3 is inserted into water and walls of the tube thus isolate part of the surface of water 1 to form an isolated surface. Again, a partial vacuum is formed when pump 5 sucks air away from the surface of the water within the tube. The vacuum leads from the water surface via holding compartment or gas cell 4 to the vacuum pump 5 which is the vacuum source.

The tube 3 may be inserted to a predetermined depth in the pond water 1, and the surface of the water 1 within the tube is isolated. The pump 5 produces the vacuum above the water surface, enhancing evaporation. The vacuum is thus filled by gas molecules evaporating from the water surface, including ammonia gas if present in the water. The extracted gas is analyzed by spectrometric, electrochemical or other methods. There is no valve to open so that the volume of water within the tube stays in equilibrium with the surroundings, and the described cycle may be repeated for dynamic updates on the state of the water. Reference is now made to FIG. 2A, which is a simplified flow chart illustrating a method of detecting dissolved gaseous impurities in an aqueous environment.

Box 10 indicates a stage of obtaining a sample volume of the aqueous environment. Box 12 is an optional stage of isolating the sample, say by closing a valve. Box 14 illustrates applying a vacuum. In particular the vacuum may be applied to the upper surface of the sample volume. The sample volume is then allowed to evaporate into the vacuum and box 16 indicates a stage of capturing the evaporation, typically passively by applying the vacuum for a predetermined amount of time. Box 18 indicates applying a measurement to the evaporate to detect a gaseous impurity. As will be discussed in greater detail below the measurement may involve spectroscopy, in particular FTIR-based spectroscopy, or other methods, including electrochemical detection methods. Finally in box 20, the measurements are used to identify the contaminant or identify the concentration of the contaminant. Contaminants of particular interest in the aquaculture environment may include ammonia. Oxygen levels may likewise be detected, so that the invention is not restricted to contaminants.

Figure 2B:
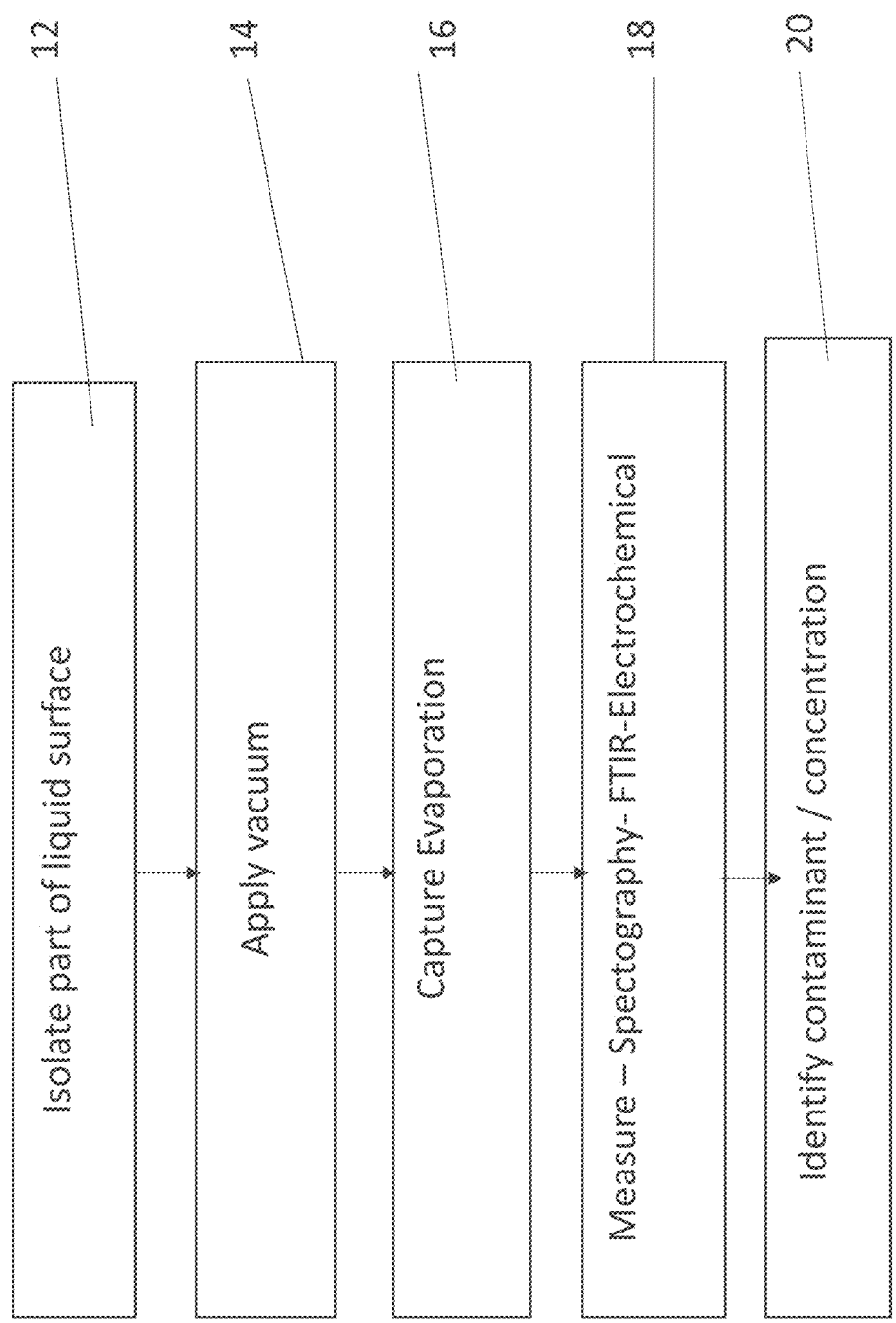
FIG. 2B is a flow chart of a variation of the methodology shown in FIG. 2A.

Reference is now made to FIG. 2B, which is a simplified flow chart illustrating a variant method of detecting dissolved gaseous impurities in an aqueous environment.

Water enters a tube to form an isolated surface indicated by box 12. Box 14 illustrates applying a vacuum to the isolated surface. Vacuum enhances evaporation from the water surface and box 16 indicates capturing of the evaporation. Box 18 indicates applying a measurement to the evaporate to detect a gaseous impurity, for example using spectroscopy. Finally in box 20, the measurements are used to identify the contaminant or identify the concentration of the contaminant or other substance of interest. Contaminants of particular interest in the aquaculture environment may include ammonia, and other substances of interest may include oxygen.

All the stages may be carried out in situ at the pond. Alternatively the sample may be obtained at the pond and the evaporation and measurement may be carried out remotely.

Alternatively, the sample may be obtained at the pond and the application of the vacuum for evaporation and the measurement may both be carried out remotely.

The embodiments are now discussed in greater detail.

Experimental Set Up and Material Preparations

Fourier Transform Infra-Red (FTIR)

MIR and FIR spectral signatures have been proven as a reliable method to characterize, identify and quantify different substances. Use of the Fourier transform infra-red technique (FTIR) provides a powerful tool capable of detecting substance fingerprints in gas, air and solid materials. Ammonia molecules are composed of a single nitrogen atom, surrounded by three hydrogen atoms. This structure, at room temperature, has a unique spectral signature in the MIR spectrum which includes three absorption lines at about 950 $cm^{-1}$ at which the H-N connection wags, at 1800 $cm^{-1}$ at which the connection H-N-H scissors, and at 3400 $cm^{-1}$ at which the H-N connection stretches. Alternative structures are available for other materials.

The FTIR spectroscopy has been proven valid for detecting $NH_3$ molecules in agricultural sites, and capable of measuring and quantifying their levels. The measurements take place in an open path system, on the gas phase of the molecule. In order to get reliable data, embodiments of the present invention may carry out measurements using several micro-windows at the same time, to avoid or minimize water vapor interference.

An embodiment of the present invention relates to monitoring changes and detecting low concentrations of toxic ammonia in fish pond water, and may further be used to remove or even eliminate other substances present in the fish pond environment. The embodiment may also determine increasing or decreasing levels of ammonia as a function of time and thus provide an alert regarding the approach of a dangerous level. Such a method relates to utilizing the uniqueness of the spectral signature of ammonia, which is characteristically different from other substances encountered in fish ponds. Ammonia has no color and consists of a molecule with a boiling point of –33° C., which therefore is commonly present as a gas. The solubility of ammonia in water is about 47% at a temperature of 0° C., and drops to about 31% at 25° C., all at a pressure of 1 bar. The ammonia molecule is lighter than air, so it tends to rise when released.

Figure 3A:
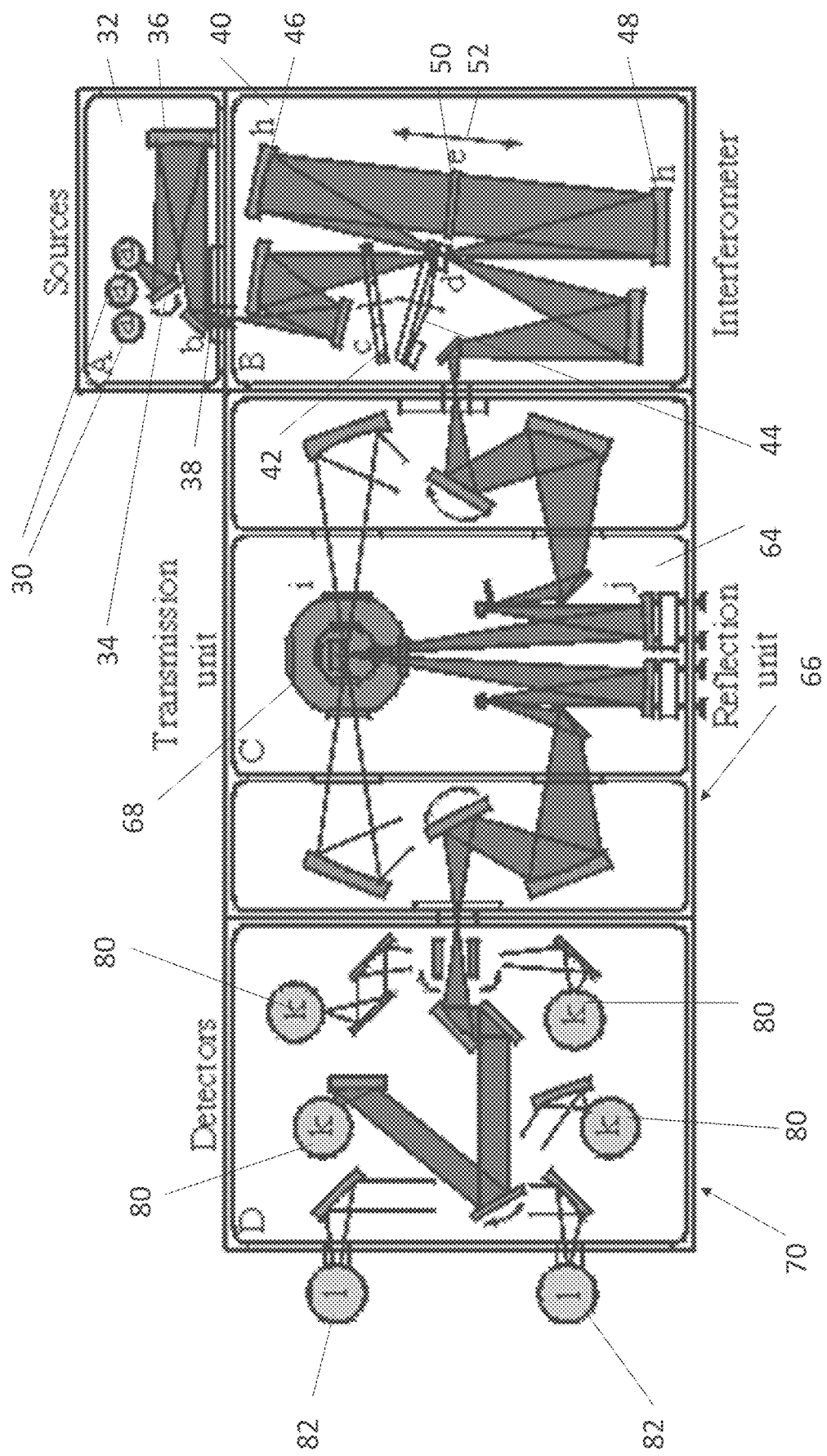
FIG. 3A is a diagram of an optical arrangement for Fourier Transform infra-red (FTIR) spectroscopy of a sample according to the present embodiments.
Figure 3B:
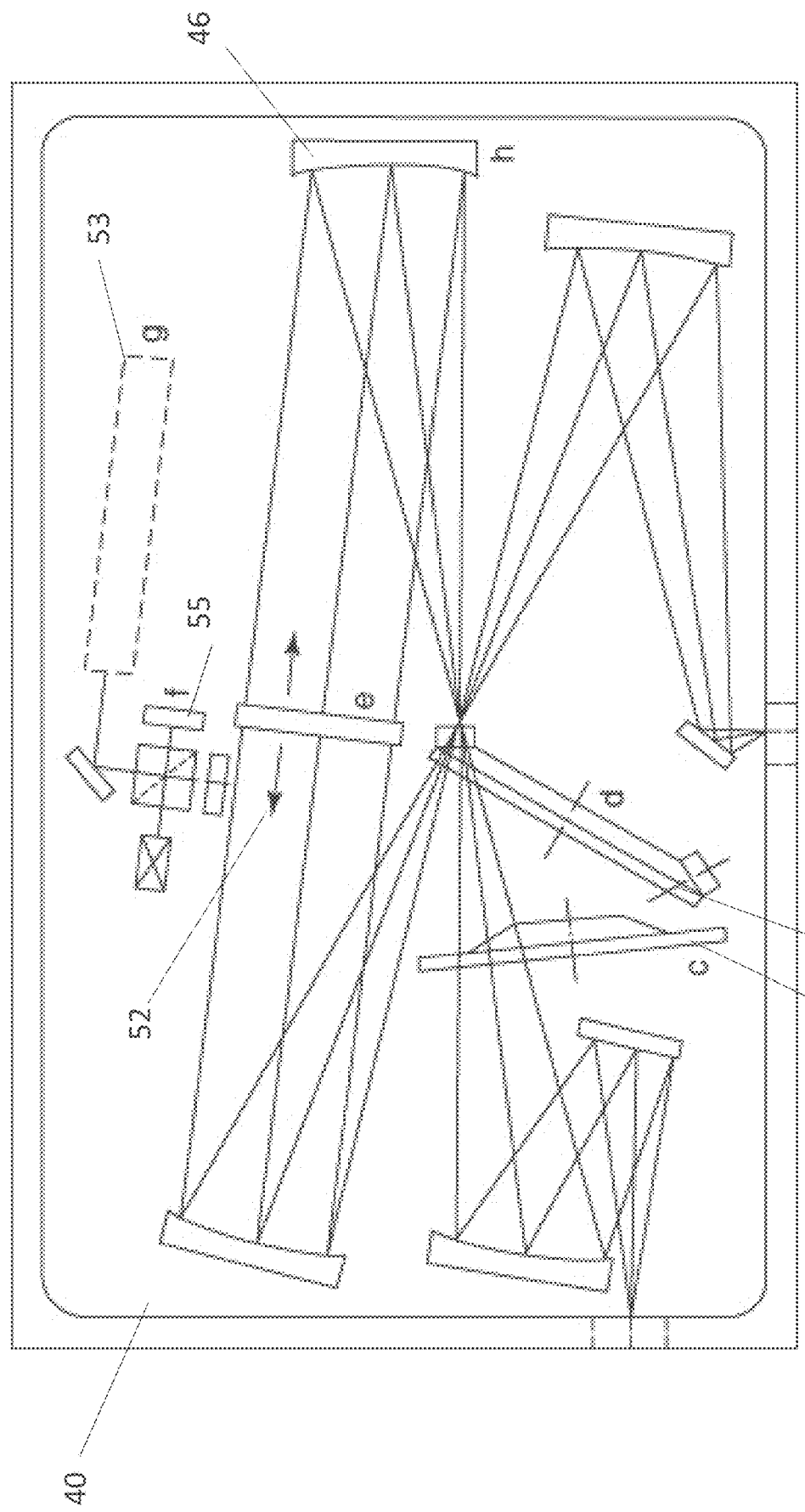
FIG. 3B is a detail of a part of FIG. 3A.

Referring now to FIGS. 3A and 3B, in the present embodiments, the spectral analysis of Ammonia absorption lines may be carried out using an FTIR spectrometer, and a BRUKER IFS-113 was used in one experimental setup, which is now described by way of example. An experimental optical scheme of the FTIR is shown in FIGS. 3A and 3B. The spectral range of the infrared spectrometer IFS 113v, which is powerful in the far- and mid-infrared frequency range, is supplemented by a quasi-optical system.

Radiation from radiation sources 30 in the chamber 32, for example a mercury, a tungsten and a Glowbar lamp, may be selected using a small rotatable mirror 34 depending on the desired frequency range.

The light passes via fixed mirror 36 and then through a variable aperture 38 into the interferometer chamber 40 which houses a Michelson interferometer. The beam is sent through a filter wheel 42 holding four different attenuators.

Afterwards the beam is split into two rays by one of six beam-splitters on second wheel 44. The split beams are then made parallel by mirrors 46 and 48. Mirror 50 is a two-sided mirror that moves as indicated by arrow 52. The moving two-sided mirror 50 changes the path difference between the two rays respectively before they are reflected back onto the corresponding beam splitter on second wheel 44. The exact position of the mirror 50 is detected by a reference interferometer using a He—Ne laser 53 and a source of white light 55 (see FIG. 3B).

Leaving the interferometer chamber 40 one can choose between two foci (i) 60 and (j) 62 to place a cryostat, oven or just the sample—reference numeral 68—in chamber 64 of reflection unit 66. This compartment enables carrying-out Transmission, Reflection and ATR measurements using a suitable accessory.

The beam continues into detector chamber 70 in which several detectors can be installed for example Mercury cadmium telluride (MCT), Indium Antimonite (InSb) and two DTGS. In the present embodiment one of the DTGS detector is used. Additionally there are flanges at the right side where two He-bolometers 82 are used if cryogenics are required. The choice depends on the desired frequency range, sensitivity, SNR and response time.

Figure 4:
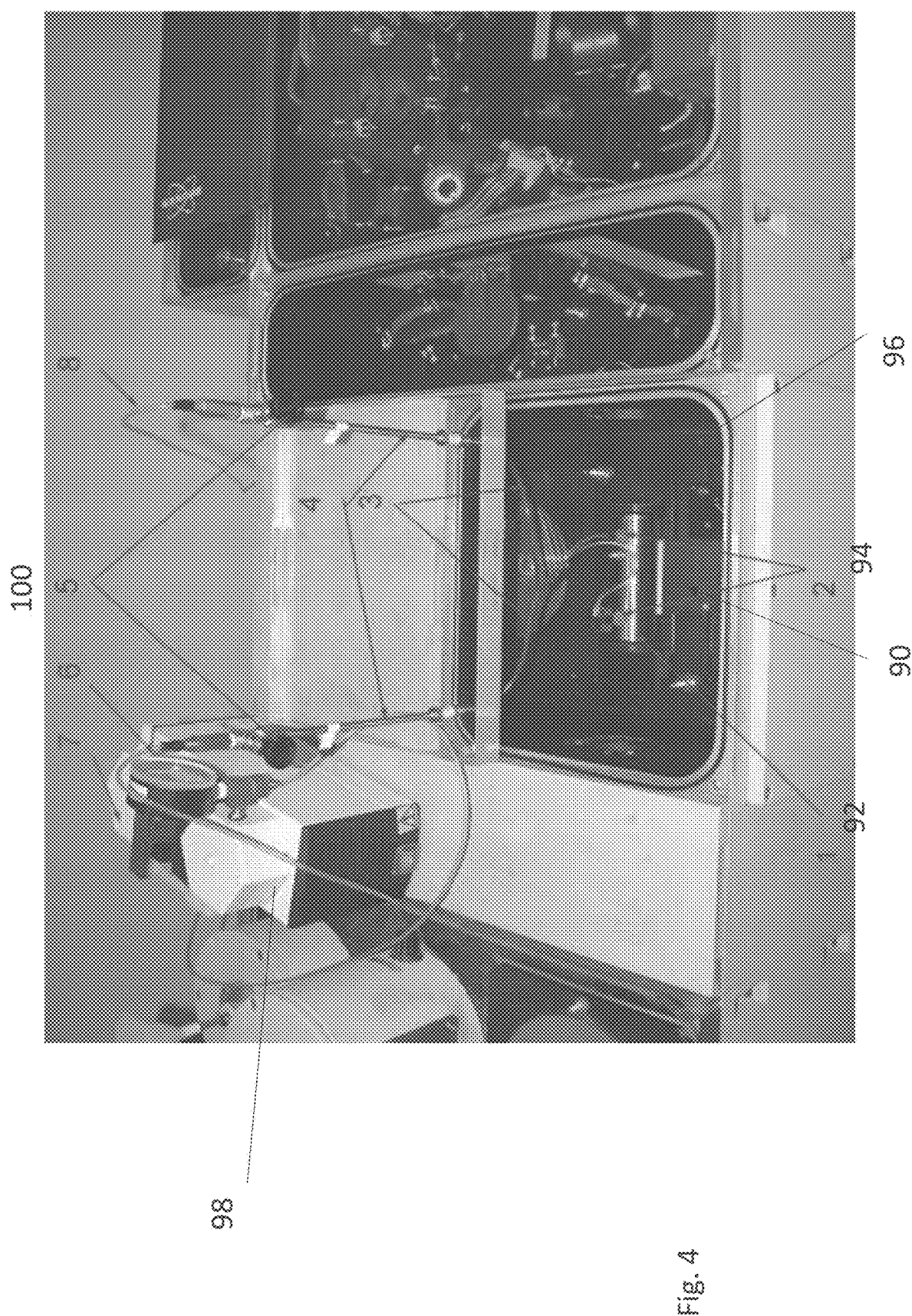
FIG. 4 is a photograph showing a gas cell inserted into a measurement device for FTIR.

Reference is now made to FIG. 4 which illustrates the compartment 4 with the gas sample being inserted into an FTIR apparatus according to FIGS. 3A and 3B. In order to measure the pond water evaporation a temperature controlled gas cell (type TGS-3-BR2) was used to contain the sample obtained according to FIG. 1A or FIG. 1B. The gas cell 90, comprising a metal body 92 and adaptors 94 at either end, is locked in the measurement chamber 96 of the FTIR. The evaporation sample is transferred to the gas cell using diaphragm vacuum pump 98.

The pump creates a vacuum at the outlet side of the assembly, while needle valves 100 are closed. When the accepted vacuum level is reached, the needle valves 100 are opened and the gas flows into the cell 90. The analyses in the MIR may be conducted in the 400 $cm^{-1}$-4000 $cm^{-1}$ band, using a Globar lamp radiation source, KBr beam splitter, ZnSe windows of 25 mm diameter and 2 mm thickness and DTGS detector. The embodiments may be capable of detecting Ammonia at low concentration levels lower than 1 PPM and as low as 0.1 ppm, indeed depending on the breed of fish in the pond, the requirement is to be able to detect concentrations of ammonia as low as 0.1 ppm.

The sensitivity of the gas cell is increased by modifying the optics so that a beam crosses the gas multiple times over the length of the gas cell. A type of gas cell known as a white cell provides oppositely facing mirrors on either side of the gas cell and a beam that is introduced to the space between the mirrors at a nearly ninety degree angle. The result is to produce some hundreds of beam crosses over the length of the gas cell. Likewise a resonator cell is an alternative possibility for providing multipath. A sensor is placed on one of the two oppositely facing mirrors, so that a potentially infinite path length is provided and there is no need for the beam ever to exit the space. The use of a multipath cell allows the measurement device to remain more compact, as a 7 m path length may be provided in a 70 cm cell. Variable path length cells may be used to provide variable sensitivity.

It is noted that a single measurement device may be used to detect multiple substances. However different substances have spectral absorption lines at different places on the electromagnetic spectrum, so a single sensor may only be possible if both the substances have absorption lines which are very close together. If the absorption lines are a little further apart then filters may be used with the single sensor. However if the absorption lines are not close together at all then separate sensors may be needed, albeit that they may be located in the same gas cell.

In the following, the testing of the above experimental setup is given by way of example.

Calibration Test:

Analyses of Ammonia in water were carried out with FTIR spectrometer Bruker IFS-113, equipped with the Temperature-Controlled Gas Cell (TGS) type TGS-3-BR2. A bottle containing 250 cc $DiH_2O$ was tested to create a zero base line (reference), and then Ammonia was added and measured at concentrations of 0.5 PPM, 1 PPM 2 PPM, 4 PPM and 10 PPM in the DiH2O. pH level was sampled at the start and at the end of the experiment, in order to quantify the $NH_3$ level in the solution. In order to achieve reliable experimental results, the measurements at every concentration were repeated 10 times. The analyses were carried out in the MIR range. The absorbance of the sample at the peak of 966 $cm^{-1}$ was calculated using the OPUS spectroscopic code of Bruker. A Globar lamp, KBr beam splitter, DTGS detector with KBr window, and 2-mm ZnSe windows in the gas cell were used.

Temperature Testing Set-Up

Figure 5:
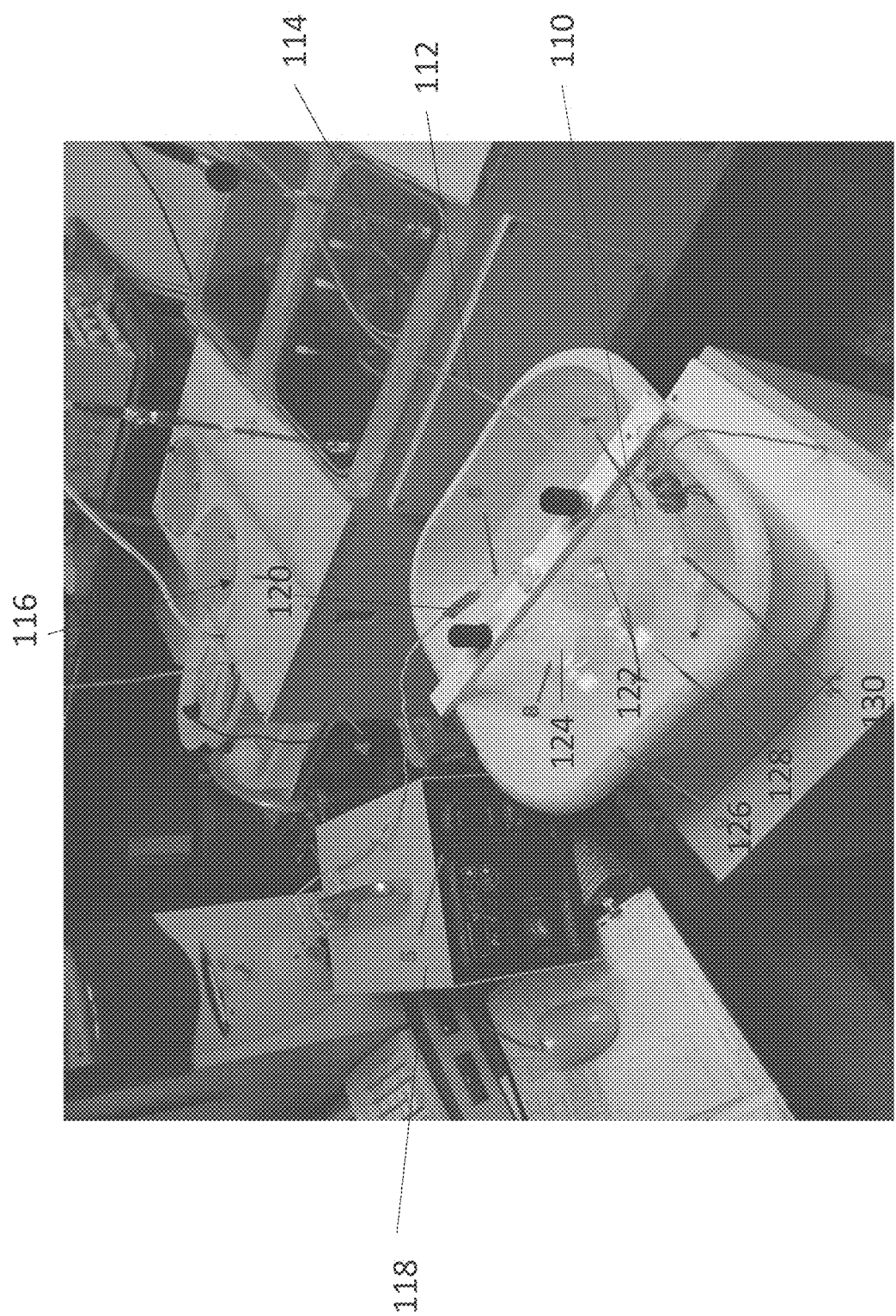
FIG. 5 is a photograph showing an experimental arrangement for controlled temperature measurement of samples according to embodiments of the present invention.

Three vacuum glass bottles (SYNF 490250 of Sigma-Aldrich) 250 cc were used in the experiment. Two bottles were filled with $DiH_2O$ water with 2.3 ppm ammonia, and the third bottle was used to monitor temperature inside the bottles. All bottles were inserted into a bath of temperature controlled water as shown in FIG. 5. At first, a bottle was filled with a sample in a manner that assures a minimum of residual air inside; then the bottle was closed hermetically; connected to the inlet of the gas cell; and the inlet valve was closed. Next, the measurement gas cell was evacuated through the outlet; and then, when the accepted vacuum (in this case about 10 mbar) was reached, the outlet was closed and the inlet was opened. The gas cell (having a volume of about 15 ml) sucked gas from the sample bottle. Those volumes became connected and hermetically isolated from the atmosphere throughout the duration of the experiment.

The experiments began with cold water (4° C.); and then the water temperature was raised by adding hot water to the container. A series of measurements were conducted while the sample temperature was increased in steps: 5, 10, 15, 20, 25, 30 and 35° C. The pH level was sampled at the end of the experiment, in order to quantify the $NH_3$ level in the solution. In order to improve the accuracy of the spectral measurements of the Ammonia content in the evaporation, the spectral measurements were repeated five times at each temperature. The analyses were carried-out at MIR range; and the absorbance of the sample was taken at the peak of 966 $cm^{-1}$ and calculated by OPUS standard spectrometric code of Bruker. The FTIR was configured to use the Globar lamp, KBr beam splitter, DTGS detector with KBr window, and 2-mm ZnSe windows in the gas cell.

As shown in FIG. 5: a hermetically sealed bottle 110 contains a sample of ammonia in water, and is connected by tube 112 with the gas cell 114 inside of the FTIR 116. The opposite valve of the gas cell is connected to a diaphragm vacuum pump (not shown). A temperature controller 118 uses a thermocouple 120 to obtain the temperature inside of bottle 122 which is the equivalent of the temperature in the sample bottle 110. The hermetically sealed bottle 124 contains the control ammonia solution which is the same as the sample. All three bottles are placed in tank 126 which is filled with water 128 to carry out a temperature controlled test. The thermometer 130 shows the temperature of water.

Experimental Results

Figure 6:
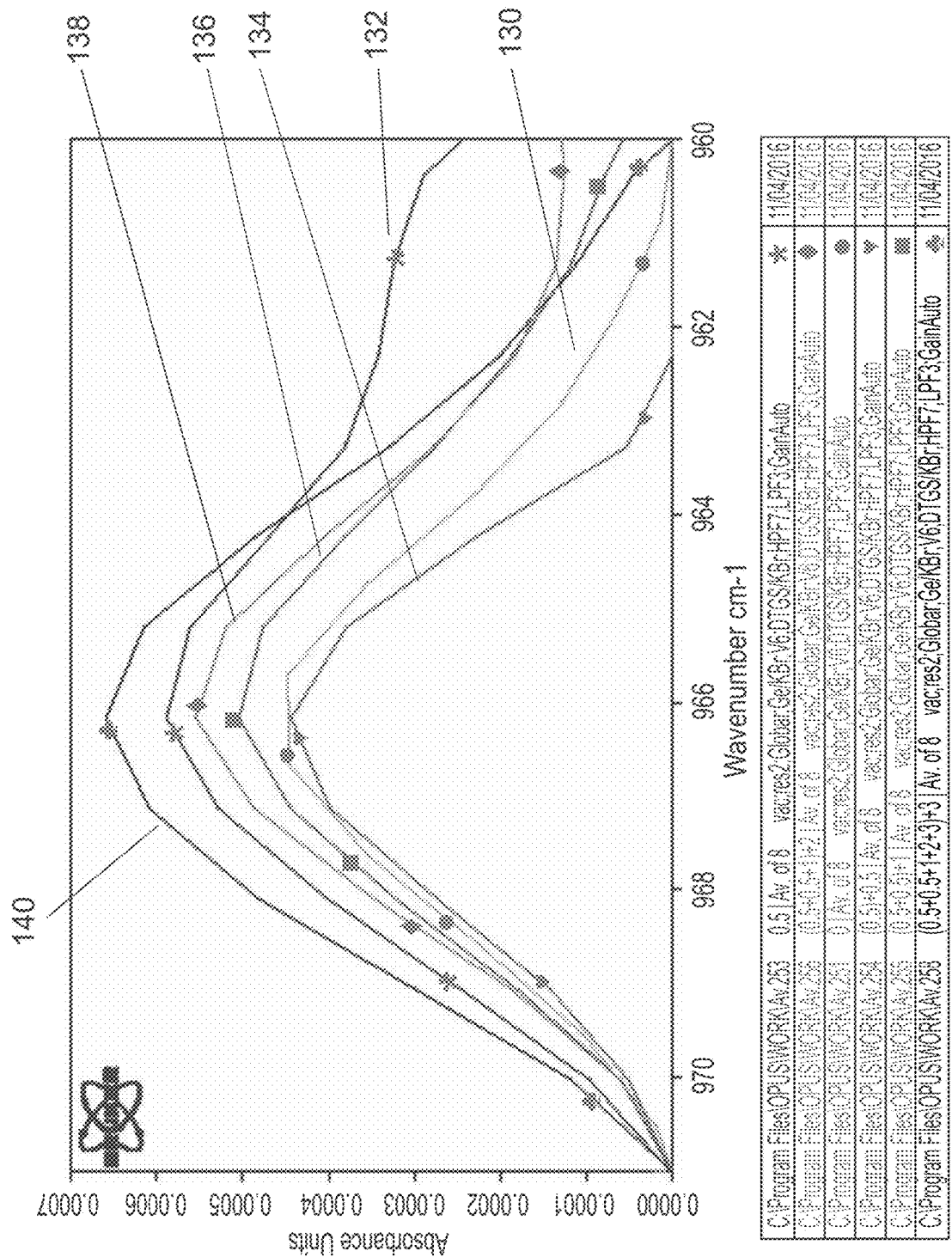
FIG. 6 is a graph showing experimental results of spectral absorption lines obtained for different ammonia concentrations using embodiments of the present invention.

Calibration Test:

The experimental spectra measurements of six different concentrations of Ammonia in $DiH_2O$ around the 966 $cm^{-1}$ absorption line are given in FIG. 6. The analyses were carried-out at MIR range; and the absorbance of the sample was taken at the peak of 966 cm-1 and was calculated by the OPUS standard spectrometric code of Bruker. Each spectrum line in the curve is an average of eight measurements. The FTIR was configured to use the Globar lamp, KBr beamsplitter, DTGS detector with KBr window, and 2-mm ZnSe windows in the gas cell.

More specifically, FIG. 6 illustrates spectra at the 966 $cm^{-1}$: line with circles 130—0 ppm of $NH_3$; line with asterisks 132—0.2 ppm; line with hearts 134—0.4 ppm; line with squares—0.8 ppm; line with diamonds 138—1.6 ppm; and line with clubs 140—4 ppm.

It can be seen that the spectra 132 of 0.2 ppm, the line with asterisks, has an unexpected shape: the right part is wider, than for all other spectra.

Figure 7:
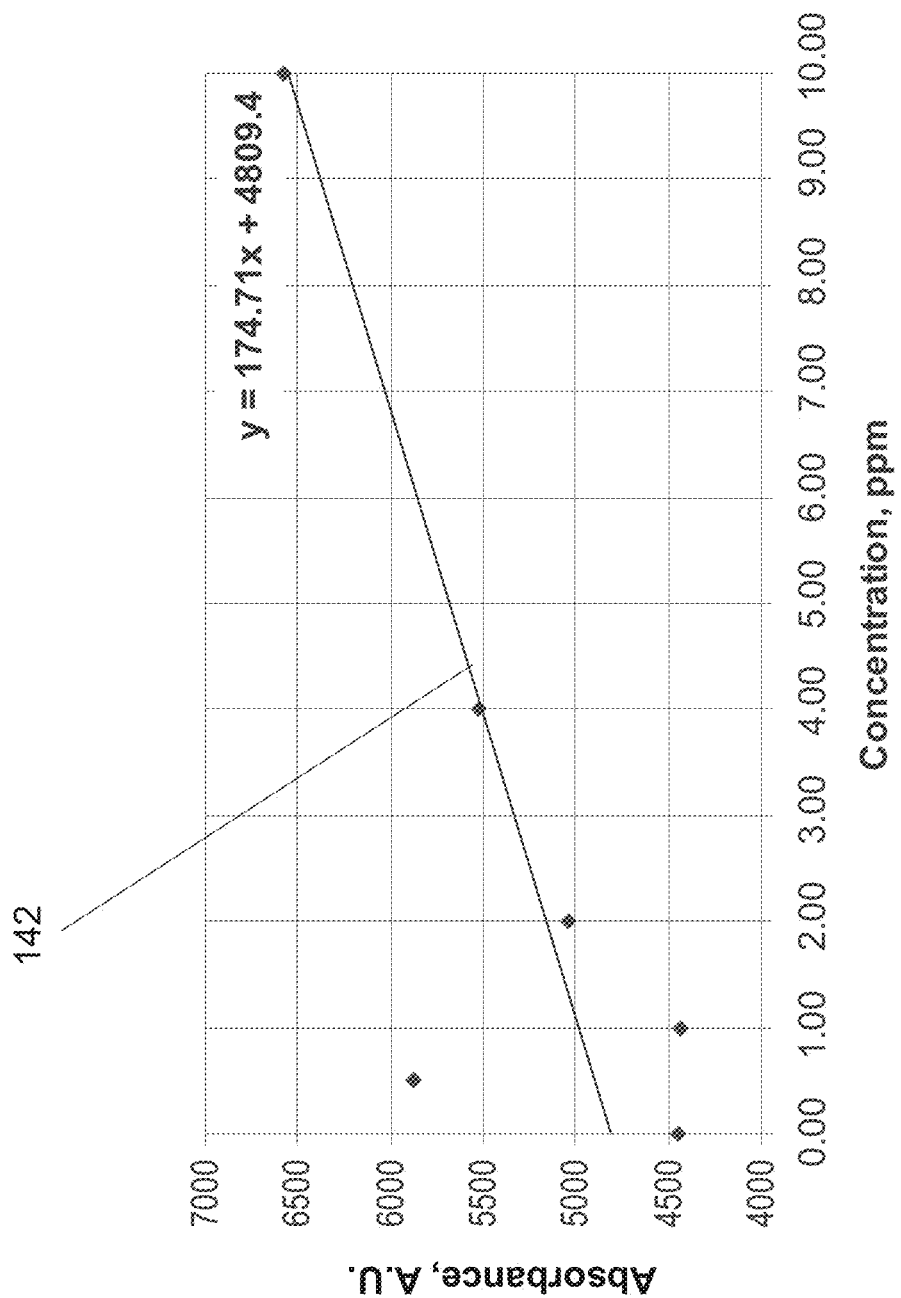
FIG. 7 is a simplified graph showing the relationship between absorption lines and ammonia concentration as determined from the graph of FIG. 6.

Calibration curves based on the results of FIG. 6 are presented in FIG. 7, and FIG. 7 shows the dependence of spectral absorbance (AU) on Ammonia concentration as straight line 142.

Figure 8:
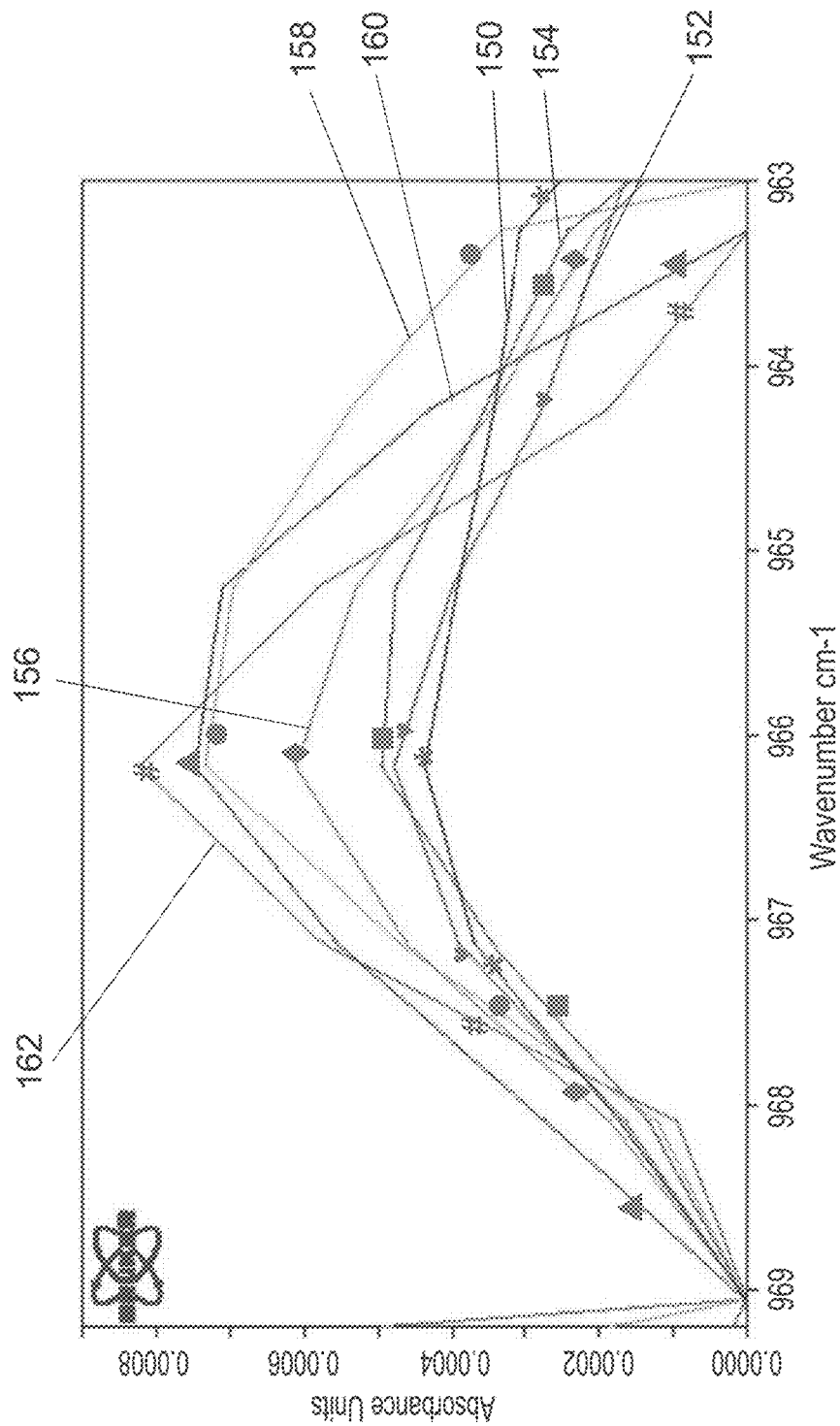
FIG. 8 is a graph showing experimental results of spectral absorption lines obtained for a single ammonia concentration at different temperatures using embodiments of the present invention.

Temperature Test:

Spectra measurements obtained for different temperatures and constant Ammonia concentration are shown in FIG. 8. Specifically, the line with asterisks 150 is for 5° C.; line with hearts 152 is for 10° C.; line with squares 154 is for 15° C.; line with diamonds 156 is for 20° C.; line with circles 158 is for 25° C.; line with triangles 160 is for 30° C.; and line with hashtags 162 is for 35° C. As seen in FIG. 8, the peak absorption values increase with the increase in the sample temperature.

Figure 9:
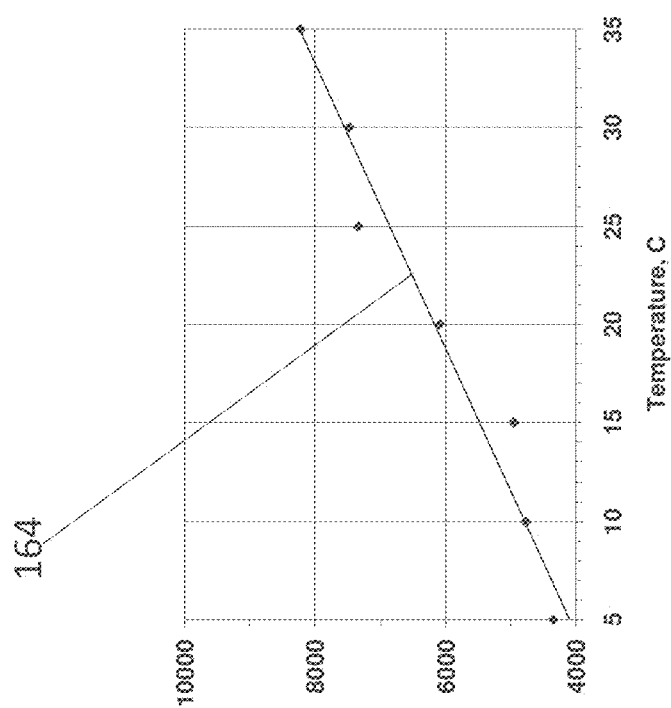
FIG. 9 is a simplified graph showing the relationship between absorption lines and temperature at fixed ammonia concentration as determined from the graph of FIG. 8.

The calculated dependence of absorption on the temperature is shown in FIG. 9 by a straight line graph 164.

The results of the temperature dependence test (see FIG. 9) show that the absorbance at the line 966 cm-1 is very close to the linear line dependence. The absorbance of the 2.3-ppm solution of ammonia in water at the 966 cm-1 line is very close to the line dependence. The middle IR signal at 966 cm-1 almost doubles with the temperature increase from 5° C. to 35° C., and the results fit expectations, since as the temperature rises more ammonia is released from the water.

In the calibration test it can be seen (FIG. 7) that the calibration line is close to the experimental points above 0.4 ppm. The calibration line for the method of vacuum extraction ammonia from the water samples at 0.4 ppm up to 4 ppm allows the determination of ammonia content with sufficient accuracy.

The present tests indicate that the present embodiments may be reliable at detecting and measuring $NH_3$ at very low concentrations in the water. The method may be utilized to detect rising ammonia levels in fish ponds in real time. The same apparatus and methodology may be used to detect concentration of other variables in the water, such as Nitrate, Nitrite and different toxins and may enable a general improvement in fish ponds water quality control.

Figure 10:
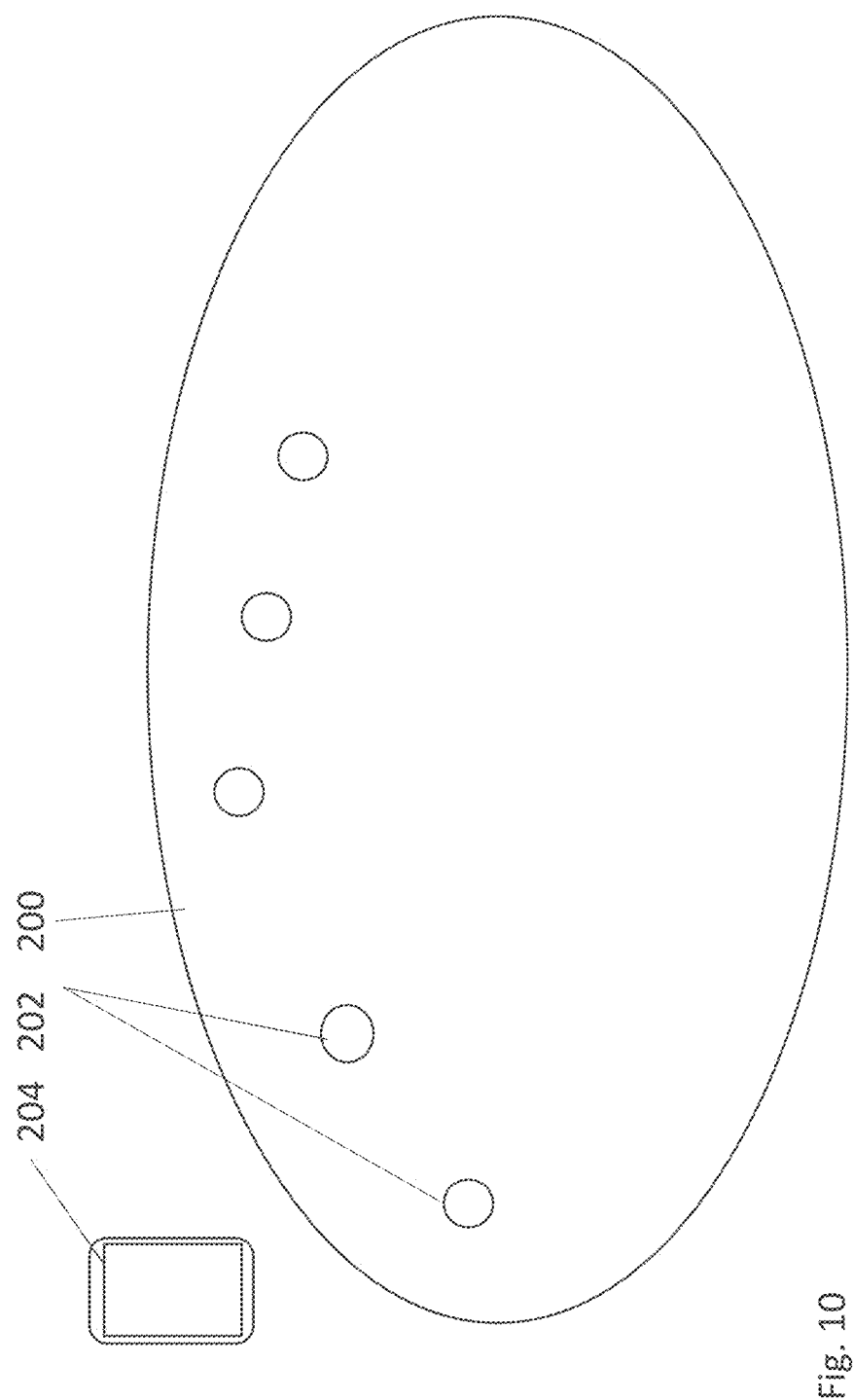
FIG. 10 is a simplified schematic diagram of multiple measuring units according to the present embodiments being deployed over a body of water.

Reference is now made to FIG. 10, which shows a body of water 200. In the body of water, which may be a fishpond or may be a length of coastline, a series of measurement devices 202 according to the present embodiments are moored or allowed to float freely. The measurement devices may include batteries or solar cells and may take measurements at regular intervals and transmit the results to a central controller 204, which may conveniently be an application running on someone's mobile telephone. In free-floating embodiments, a GPS system may be included with each device so that the location can be reported along with the measurement. The moored embodiments may either use GPS or simple identification of the devices, whichever is more convenient.

Thus the body of water may be monitored in real time. In the case of a fishpond, fresh water may be added to the pond before the fish start to feel the ill effects. In the case of a river or coastline, an increase in ammonia is an indication of a pollution event such as illegal sewage discharge. Real time detection of the pollution event allows for a faster and thus more effective reaction.

It is expected that during the life of a patent maturing from this application many relevant spectroscopy techniques and equipment will be developed and the scope of the corresponding terminology is intended to include all such new technologies a priori.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. Apparatus for detecting a dissolved gaseous impurity in an aqueous environment, comprising:

an opening for liquid of said aqueous environment;

a vacuum pump located to exert a vacuum onto said liquid, to cause evaporation from said liquid into said vacuum; and a holding compartment for holding evaporated gas from said sample, the holding compartment being removable for remote spectroscopic analysis.

2. The apparatus of claim 1, further comprising a spectroscopy unit configured to detect spectroscopic signals of said evaporated gas, thereby to identify a gaseous impurity or a concentration of said gaseous impurity in said aqueous environment.

3. The apparatus of claim 2, wherein the spectroscopy unit comprises a radiation source and a detector.

4. The apparatus of claim 2, wherein the spectroscopy unit is configured to use Fourier Transform Infra-Red (FTIR) spectroscopy.

5. The apparatus of claim 1, further comprising an MID IR detector unit configured to identify said gaseous impurity.

6. The apparatus of claim 1, comprising a sampler for holding a sample of said liquid, the sampler having a first end and a second end and being vacuum resistant, wherein said sampler comprises a valve at said first end, the valve being openable to obtain said sample and closeable prior to applying said vacuum to a surface of said sample from said second end.

7. The apparatus of claim 2, wherein said detector unit is configured to detect ammonia or a concentration of ammonia or other dissolved substances.

8. The apparatus of claim 1, wherein the aqueous environment is an aquaculture environment.

9. A method of detecting dissolved gaseous impurities in an aqueous environment, comprising:
obtaining an isolated surface of the aqueous environment;
applying a vacuum above the isolated surface to cause evaporation from said surface; and
remotely applying measurement to said vacuum to detect a gaseous impurity.

10. The method of claim 9, wherein said measurement is obtained using MIR detection.

11. The method of claim 9, wherein said measurement is obtained using spectroscopy.

12. The method of claim 11, wherein said measurement is obtained using Fourier Transform Infra-Red (FTIR) spectroscopy.

13. The method of claim 10, used to detect a concentration of ammonia.

14. The method of claim 9, wherein said aqueous environment is an aquaculture environment.

15. The method of claim 9, wherein said aqueous environment is a liquid for human consumption.

16. A method of monitoring a body of water for a contaminant comprising:
placing within said body of water a plurality of monitoring devices, each device comprising:
an opening for liquid of said aqueous environment;
a vacuum pump located to exert a vacuum onto said liquid, to cause evaporation from said liquid into said vacuum; and
a holding compartment for holding evaporated gas from said sample; and
at a remote location collecting measurements from each of said monitoring devices.

17. The method of claim 16, comprising mooring at least some of the monitoring devices.

18. The method of claim 16, comprising free-floating at least some of the monitoring devices.

19. The method of claim 16 comprising providing location and transmission capability to at least some of the monitoring devices.

20. The method of claim 16, comprising collecting said measurements at predetermined intervals.

21. The method of claim 16, comprising providing a battery or a solar cell to at least some of the monitoring devices.

* * * * *